United States Patent [19]

Sundeen

[11] 4,321,270
[45] Mar. 23, 1982

[54] SUBSTITUTED CHROMANS

[75] Inventor: Joseph E. Sundeen, Yardley, Pa.

[73] Assignee: E. R. Squibb & Sons, Inc., Princeton, N.J.

[21] Appl. No.: 229,415

[22] Filed: Jan. 29, 1981

[51] Int. Cl.³ .................. A61K 31/445; C07D 405/04; C07D 405/06
[52] U.S. Cl. .................... 424/267; 546/196; 546/269; 544/376; 260/345.5; 424/263; 424/250; 424/283
[58] Field of Search .......... 546/196; 424/267

[56] References Cited

U.S. PATENT DOCUMENTS 3,419,560 12/1968 Bernstein et al. ............... 546/196
4,153,796  5/1979 Hoehn ............................ 546/120
4,214,081  7/1980 Krapcho ........................ 542/424
4,237,162 12/1980 Kabbe et al. .................. 424/283

FOREIGN PATENT DOCUMENTS 1296431 11/1972 United Kingdom .

OTHER PUBLICATIONS

Lehninzer in Biochemistry, Second Edition, Worth Publishers, Inc. Copyright 1975, pp. 357 and 358.

Primary Examiner—Henry R. Jiles
Assistant Examiner—Jane T. Fan
Attorney, Agent, or Firm—Lawrence S. Levinson; Burton Rodney

[57] ABSTRACT

The invention relates to chroman derivatives of the general formula

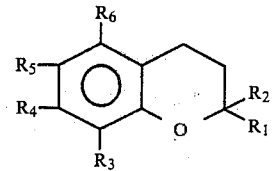

wherein
$R_1$ is hydrogen, lower alkyl, substituted phenyl, phenyl, phenyl-lower alkyl, substituted phenyl-lower alkyl or lower alkyl-amino-lower alkyl;
$R_2$ is

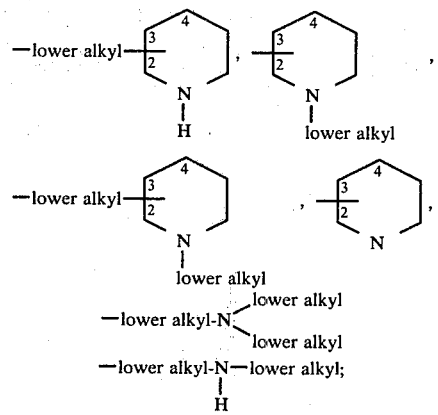

$R_3$, $R_4$, $R_5$ and $R_6$ each is independently selected from hydrogen, hydroxy, amino, -o-acyl, -o-lower alkyl;

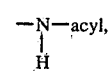

halogen, lower alkyl, or halo substituted lower alkyl; and salts and hydrates thereof.

These compounds are useful as anti-inflammatory agents; for inhibition of blood platelet aggregation, as antiallergy and as antihypertensive agents.

12 Claims, No Drawings

SUBSTITUTED CHROMANS

BACKGROUND OF THE INVENTION

Lehninger Biochemistry, Second Edition, Copyright 1975, pages 357 and 358 discusses Vitamin E as having first been recognized as a factor in vegetable oil that restores fertility in rats grown on cows milk alone and otherwise incapable of bearing young. Vitamin E has the formula

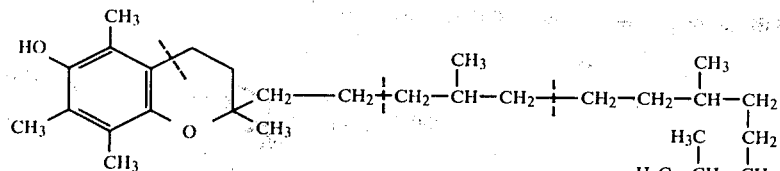

Green, et al. in U. K. Patent No. 1296431 discloses phenoxyalkylaminomethyl chromans of the formula

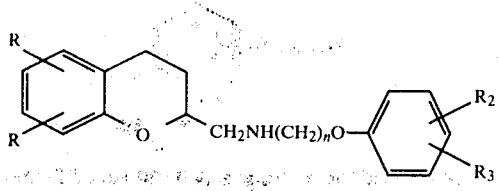

where R and R' are hydrogen or halogen atoms or alkyl or alkoxy groups containing 1 or 2 carbon atoms, n is an integer of from 2 to 6 and $R^2$ and $R^3$ are hydrogen atoms or alkyoxy groups containing 1 or 2 carbon atoms.

SUMMARY OF THE INVENTION

The invention relates to chroman derivatives of the general formula

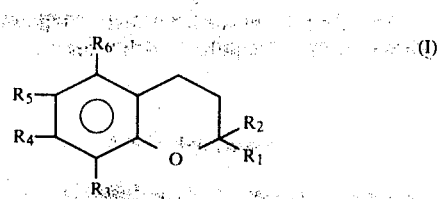
(I)

wherein $R_1$ is hydrogen, lower alkyl, substituted phenyl, phenyl, phenyl-lower alkyl, substituted phenyl-lower alkyl or lower alkyl-amino-lower alkyl;

$R_2$ is

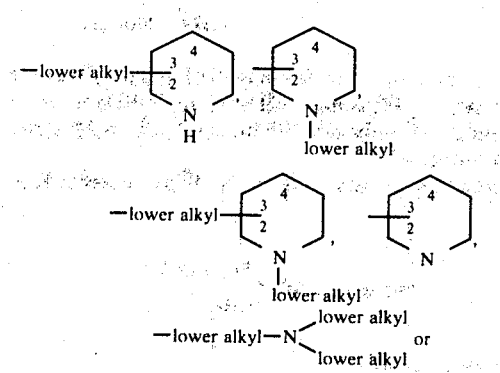

—lower alkyl—N—lower alkyl;
            |
            H $R_3$, $R_4$, $R_5$ and $R_6$ each is independently selected from hydrogen, hydroxy, amino, -o-acyl, -o-lower alkyl;

—N—acyl,
 |
 H

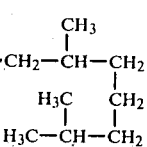

halogen, lower alkyl, or halo substituted lower alkyl; and salts and hydrates thereof.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1-15 carbon atoms, preferably 1-10 carbon atoms. Examples of the type of groups contemplated are methyl, ethyl, propyl, isopropyl, butyl, t-butyl, nonyl, etc.

The halogen groups include chlorine, bromine, iodine and fluorine.

The phenyl-lower alkyl groups include the lower alkyl groups as defined above attached to a phenyl, e.g. benzyl, phenethyl.

The substituted phenyl and substituted phenyl-lower alkyl groups include one or two (preferably only one) simple substituent selected from halogen (preferably chlorine and bromine), lower alkyl and -o-lower alkyl, e.g. 2,3 or 4 chlorophenyl; 3,4-dichlorophenyl, 2-methylphenyl.

The compounds of formula I may be formed from compounds of the formula:

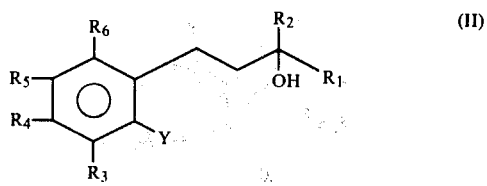
(II)

wherein Y is —$OCH_3$ or —OH.

When Y is —$OCH_3$ the compound of formula II is treated with hydrobromic acid and acetic anhydride to form the formula I compound.

When Y is —OH the compound of formula II is treated with concentrated hydrochloric acid and heated to form the formula I compound.

By hydrolysis of these formula I products additional formula I products are obtained.

Alternatively, the formula I compounds may be formed from compounds of the formula

[Structure III: benzene ring with OH, R3, R4, R5, R6 substituents and CH(R1)N(CH3)2 group] (III)

by reacting the formula III compound with a compound of formula $R_2$—CH═CH$_2$ (IV)

while refluxing in mesitylene.

The compounds of formula II may be formed by reacting a compound of the formula

[Structure V: benzene ring with R3, R4, R5, R6, OCH3 substituents and CH2CH2C(=O)R1 group] (V)

with a compound of the formula $R_2$MgCl(grignard). (VI)

The compound of formula V may be formed by treating a compound of the formula

[Structure VII: benzene ring with R3, R4, R5, R6, OCH3 substituents and CH=CH−C(=O)R1 group] (VII)

with hydrogen in the presence of a catalyst such as platinum oxide.

Compounds of the formula (VII) may be formed from compound of the formula

[Structure VIII: benzene ring with R3, R4, R5, R6, O—CH3 substituents and CHO group] (VIII)

by treatment with a compound of the formula $$CH_3-\overset{O}{\underset{\|}{C}}-R_1$$ (IX)

in base.

Alternatively, the compounds of formula II may be formed by reacting a compound of the formula

[Structure X: benzene ring with R3, R4, R5, R6, OCH3 substituents and CH2CH2C(OH)(R1)(lower alkyl)−pyridine] (X)

by catalytic hydrogenation.

Compounds of formula (X) may be formed from compounds of formula (V) by reacting it with a compound of the formula

[Structure XI: Li⊕ ⊖lower alkyl−pyridine (positions 2,3,4)] (XI)

Compounds of formula I wherein $R_2$ is

[Structure: −lower alkyl−piperidine with N−lower alkyl]

may be formed by treating a compound of formula I wherein $R_2$ is

[Structure: −lower alkyl−piperidine with N−H]

(obtained by the procedure using compounds X and XI above) with a compound of the formula $$\text{lower alkyl}-\overset{O}{\underset{\|}{C}}-Cl$$ (XII)

to form a compound of the formula

[Structure XIII: chroman ring system with R3, R4, R5, R6 substituents, lower alkyl, R1, and piperidine-N−C(=O)−lower alkyl] (XIII)

A compound of formula I may be formed by treating the compound of formula (XIII) first with BH$_3$ and then with acid and finally with dilute base such as NH$_4$OH, and barbituric acid.

Alternatively, compounds of formula I wherein $R_2$ is $$-\text{lower alkyl}-N\begin{smallmatrix}\text{lower alkyl}\\\text{CH}_3\end{smallmatrix}$$

may be treated with

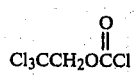

and then with Zn and acetic acid to form compounds of the formula

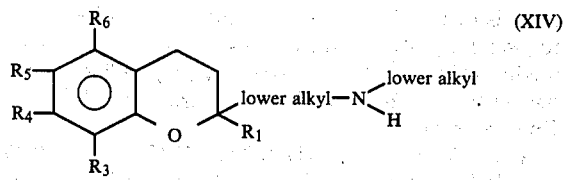

Treating the compounds of formula XIV with

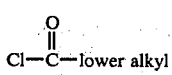

yield a compound of the formula

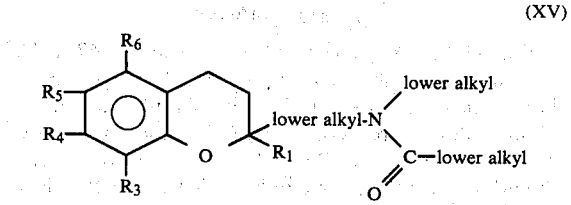

By treating the compound of formula XV with BH$_3$ in tetrahydrofuran and then HCl while heating gives a compound of formula I wherein R$_2$ is

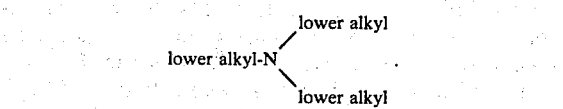

By treating compounds of formula I wherein R$_3$–R$_6$ is hydrogen, with acetic anhydride and nitric acid then compounds of the formula

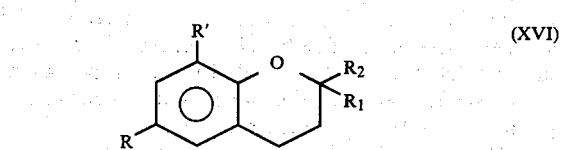

wherein R is —NO$_2$ or hydrogen and R' is —NO$_2$ or hydrogen. are formed.

By treating these with hydrochloric acid and stannous chloride formula I compounds wherein R$_3$ and R$_5$ are each independently —NH$_2$ or hydrogen are formed.

A method of forming compounds of formula III is to treat a compound of the formula

with dimethylamine and hydrogen before treatment with a compound of the formula (IV) i.e.

$$H_2C=CH-R_2$$

The compounds of formula I, and the pharmaceutically acceptable salts thereof, can be used for the treatment of inflammation in mammalian species such as mice, dogs, cats, monkeys, etc. Joint tenderness and stiffness (in conditions such as rheumatoid arthritis) are relieved by the compounds of this invention. Formulation of the compounds can be carried out according to accepted pharmaceutical practice in oral dosage forms such as tablets, capsules, elixirs or powders, or in injectable form in a sterile vehicle. The compounds of this invention can be administered in amounts of about 0.1 to 2.0 grams per 70 kilograms of animal body weight per day, preferably about 0.1 to 1.0 gram per 70 kilograms of animal body weight per day.

The compounds of this invention also have anti-allergy activity. They inhibit the effects of certain antigen-antibody reactions and, in particular, inhibit the release of mediators such as histamine. The activity of these compounds is demonstrated by the reaginic antibody induced passive cutaneous anaphylaxis (PCA) reaction in rats. [See Bach, Immediate Hypersensitivity: Laboratory Models and Experimental Findings, Ann. Rep. Med. Chem. 7, 238–248 (1972)]. These compounds also show anti-bronchoconstrictor activity without marked concomitant cardiovascular effects as shown in histamine induced bronchospasm in pithed guinea pigs.

The compounds of formula I are therefore useful in treating various allergic conditions in mammalian species such as mice, cats, dogs, etc., when administered in amounts ranging from about 0.3 to about 300 milligrams per kilogram per day. The compounds can be used to alleviate or relieve various allergic disorders and in particular to treat certain types of asthma, hayfever, rhinitis and/or other conditions involving bronchoconstriction. A preferred dosage is about 3 milligrams to about 100 milligrams per kilogram per day administered in a single dose or two to four divided doses.

A compound of formula I can be administered by the inhalation of an aerosol or powder as described in U.S. Pat. No. 3,772,336 (i.e., breathing finely divided particles of the active ingredient into the lungs), or orally or parenterally. Powders can be prepared by comminuting the active ingredient with a similarly comminuted diluent such as starch or lactose. Suitable forms for oral administration include capsules, tablets, and syrups, and a suitable form for parenteral administration is a sterile injectable. Such unit dosage forms are prepared by compounding with a conventional vehicle, excipients, binders, preservatives, stabilizers, flavoring agents or the like as called for by acceptable pharmaceutical practice. For oral administration, for example, the active substance can be combined with an inert diluent or with an assimilable edible carrier or it can be enclosed in hard or soft gelatin capsules or compressed into tablets. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a dosage as described above is obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate, and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following examples further illustrate and represent preferred embodiments of the invention. All temperatures are expressed in degrees centigrade.

EXAMPLE 1

2-[(3,4-Dihydro-2-methyl-2H-benzopyran-2-yl)-methyl]piperidine, oxalate salt (2:1)

(a)

α[2-(2-Methoxyphenyl)ethyl]-α-methyl-2-piperidineethanol

A solution of 0.2 moles of α-picoyl lithium in 500 ml of ether is prepared by adding 0.2 moles of α-picoline (18.6 g) to 0.2 moles of phenyllithium in 500 ml ether, and stirred for 15 minutes at 25° C. This solution is treated with 35.6 g (0.2 moles) of 4-(2-methoxyphenyl)-2-butanone in 200 ml ether. The viscous curdy mass is refluxed for 2 hours, cooled, and treated with saturated ammonium chloride. The organics are separated and dried with potassium carbonate and evaporated to oil containing ketone and α-picoline. This is dissolved in 5% HCl and extracted with a hexane-ether mixture. The aqueous is neutralized to pH 6 with 10% sodium hydroxide and extracted with chloroform. The organics are washed with 10% sodium hydroxide, dried (sodium carbonate) and evaporated to 35 g of an oil (65%) containing no α-picoline or ketone.

Since the oil will not crystallize it is converted to the oily hydrochloride (HCl in isopropanol to an ether solution of the free base), taken up in 200 ml of methanol and hydrogenated over 0.7 g of platinum oxide at 50 psi. The catalyst is filtered, and solvent evaporated. The oil is basified with hydroxide, extracted with chloroform, dried (potassium carbonate) and evaporated to oily free base. Ether (about 100 ml) is added and a solid crystallized (5.5 g, 16%). The mother liquors contained presumably a mixture of diasteriomers and is used in part (b) of Example 1.

The crystalline solid (2.5 g) was recrystallized from dichloromethanehexane to give α-[2-(2-methoxyphenyl)ethyl]-α-methyl-2-piperidineethanol mp 115°–116° C.

Anal. Calcd. for $C_{17}H_{29}NO_2$: C, 73.60; H, 9.81; N, 5.05. Found: C, 73.35; H, 9.78; N, 4.96.

(b)

2-[(3,4-Dihydro-2-methyl-2H-benzopyran-2-yl)-methyl]piperidine, oxalate salt (2:1).

Mother liquors made as in part (a), (24 g) are taken up in 200 ml of glacial acetic acid and treated with 100 ml of 48% HBr. After refluxing for 3 hours under nitrogen the mixture is evaporated to an oil, basified (sodium hydroxide), extracted with chloroform, dried (potassium carbonate) and evaporated to 20 g of oil. This is chromatographed on 200 g of alumina (basic, activity I) in chloroform. Intermediate fractions (500 ml) give 12 g (57%) of single spot oily chroman.

The chroman free base (2.5 g, 0.01 mole) in isopropyl ether is treated to pH 8 with oxalic acid in isopropanol to give 1.4 g (47%) of a white solid 2-[(3,4-dihydro-2-methyl-2H-benzopyran-2-yl)-methyl]-piperidine, oxalate salt (2:1) which is dried overnight at 110° over $P_2O_5$ in vacuo.

Anal. Calcd. for $C_{16}H_{23}NO.0.5\ C_2H_2O_4$ with 0.25 mole $H_2O$: C, 69.24; H, 8.37; N, 4.75. Found: C, 69.32; H, 8.37; N, 5.17.

EXAMPLE 2

3,4-Dihydro-2-methyl-2-(2-piperidinylmethyl)-2H-1-benzopyran-6-ol, hydrobromide (1:1)

(a)

α-[2-(2,5-Dimethoxyphenyl)ethyl]-α-methyl-2-piperidineethanol

Phenyl lithium is generated by reacting 47 g (0.3 moles) of bromobenzene with 4.2 g (0.61 g-atom) of lithium in 1 liter of ether. To this reagent is added 33 g (0.36 moles) of α-picoline, and the resulting mixture refluxed for 0.5 hour. Then 41 g (0.2 moles) of 4-(2,5-dimethoxyphenyl)-2-butanone is added, and the slurry stirred and heated for one hour. The mixture is cooled and treated with excess saturated ammonium chloride. The organics are separated and the aqueous reextracted with ether. The organics are shaken with excess 5% HCl, and the aqueous extracted with ether. The acidic aqueous are basified and extracted with ether, the extracts dried (potassium carbonate) and evaporated to an oil containing α-picoline. This is dissolved in 10% HCl and basified with sodium hydroxide solution until just before the α-picoline comes out of solution. Ether extractions give 40 g (66%) of oil.

An 80 g sample of the above adduct is taken up in 600 ml of methanol and acidified with HCL in isopropanol. Platinum oxide (1 g) is added and the mixture hydrogenated at 50 psi overnight. The catalyst is filtered and the solvent stripped. The free base is liberated with hydroxide, extracted with ether, and dried over potassium carbonate. Evaporation gives an oil which is chromatographed on 500 g of activity I neutral alumina in chloroform to give six 200 ml fractions. These are evaporated and then boiled with hexane, the solvent decanted and cooled to give sticky solids. The mother liquors are decanted and the solids washed with ether to give 7 g of solid, plus another 2 g as a second crop from the decanted hexane solutions, for a total of 9 g (11%) of α-[2-(2,5-dimethoxyphenyl)ethyl]-α-methyl-2-piperidineethanol. (a first isomer)

A 2 g sample is recrystallized from hexane to give the analytical sample, m.p. 101°–103° C.

Anal. Calc'd. for $C_{18}H_{29}NO_3$: C, 70.32; H, 9.51; N, 4.56. Found: C, 70.44; H, 9.66; N, 4.46.

All the mother liquors from the isolation of the first isomer are combined in ether and applied to 500 g of activity I neutral alumina. Elution completed with 1.5 liters of hexane (3 fractions) and 1 liter of chloroform (1 fraction). The second hexane fraction gives 3.5 g of white solid, and evaporation of the chloroform, boiling with hexane and working the resulting solid with ether gives 4.5 g. Another 1.5 g of solids from the mother liquor gives a total of 9.5 g (12%) of (a second isomer).

Recrystallization from dichloromethane-hexane, and then from hexane gives a solid α-[2-(2,5-dimethoxyphenyl)ethyl]-α-methyl-2-piperidineethanol, m.p. 85°–90° C.

Anal. Calc'd. for $C_{18}H_{29}NO_3$: C, 70.32; H, 9.51; N, 4.56. Found: C, 70.56; H, 9 60; N, 4.50.

(b) 3,4-Dihydro-2-methyl-2-(2-piperidinylmethyl)-2H-1-benzopyran-6-ol, hydrobromide (1:1)

A 7 g sample of α-[2-(2,5-dimethoxyphenyl)ethyl]-α-methyl-2-piperidineethanol (0.23 moles) was refluxed for 3 hours in a mixture of 100 ml of acetic acid and 50 ml of 48% HBr, then evaporated completely to dryness, and finally with benzene to remove traces of water. The oil was covered with 200 ml of acetonitrile and gave 0.8 g of solid on standing. The mother liquor is stripped, taken up in methanol-acetonitrile 1:2, treated with decoloring carbon, filtered, and diluted with ethyl acetate to give 1 g of solid, for a total of 1.8 g (23%) crystalline hydrobromide.

The solid is taken up in 40 ml of acetonitrile containing some methanol, then boiled down to 20 ml (all methanol removed) and cooled to give 1.2 g of off-white crystals of 3,4-dihydro-2-methyl-2-(2-piperidinylmethyl)-2H-1-benzopyran-6-ol, hydrobromide (1:1) m.p. 218°–221° C.

Anal. Calc'd. for $C_{16}H_{23}NO_2 \cdot HBr$: C, 56.15; H, 7.06; N, 4.09; Br, 23.35. Found: C, 56.35; H, 6.92; N, 4.20; Br, 23.13.

EXAMPLE 3

α-[3-(Dimethylamino)propyl]-α-[2-(hydroxyphenyl)ethyl]-1-methyl-4-piperidinemethanol, hydrochloride (1:2)

(a) 3-(2-Hydroxyphenyl)-1-(1-methyl-4-piperidinyl)-1-propanone

Coumarin (30 g, 0.205 moles) is reduced on the Parr apparatus in 200 ml ethyl acetate with 1 g platinum oxide at 40 psi. When the uptake ceased (ca. 1 hr.) the catalyst is removed by filtration and the filtrate evaporated to give a quantitate yield of dihydrocoumarin.

The Grignard reagent of 4-chloro-N-methylpiperidine (60 g, 0.47 moles) is prepared as in Example 3A. To this is added a solution of 23 g (0.155 moles) dihydrocoumarin in 100 ml tetrahydrofuran over 20 minutes (reaction is refluxed). Refluxed for 3½ hours. The flask is cooled in an ice bath and saturated ammonium chloride solution is added (200 ml). The layers are separated and the aqueous extracted with tetrahydrofuran. The organics are dried (magnesium sulfate) and evaporated. The residue, after an acid-base extraction, yield 13 g from the organics. Carbon dioxide is bubbled through the aqueous which is then extracted with dichloromethane. These organics are dried and evaporated to yield 26 g. Chromatography (basic alumina, activity III, chloroform) afforded 17.7 g (46%) crystalline keto-phenol.

Recrystallization of 1.6 g from dichloromethanehexane afforded the analytical sample, 1 g of 3-(2-hydroxyphenyl)-1-(1-methyl-4-piperidinyl)-1-propanone, m.p. 99°–101°.

Anal. Calc'd. for $C_{15}H_{21}NO_2$: C, 72.84; H, 8.56; N, 5.66. Found: C, 72.67; H, 8.70; N, 5.53.

(b) α-[3-(Dimethylamino)propyl]-α-[2-(2-hydroxyphenyl)ethyl]-1-methyl-4-piperidinemethanol, hydrochloride (1:2)

To a solution of the Grignard reagent of dimethylaminopropyl chloride (12.2 g, 0.1 moles) stirred in 75 ml tetrahydrofuran under nitrogen at 0° C. is added a solution of 7.6 g (0.0308 moles) of 3-(2-hydroxyphenyl)-1-(1-methyl-4-piperidinyl)-1-propanone in 50 ml tetrahydrofuran. When addition is complete, reaction allowed to warm to room temperature and then refluxed for 3½ hours. The reaction is cooled in an ice bath and saturated ammonium chloride solution (60 ml) added. This is acidified (10% hydrochloric acid) and the layers separated. The aqueous is basified (10% sodium hydroxide) and carbon dioxide bubbled in. This is extracted with dichloromethane. The organics are dried (magnesium sulfate) and evaporated. Chromatography of the residue (250 g basic alumina Act. III in chloroform and 5% methanol in chloroform) yielded 7.7 g (61%) diol adduct.

A sample (3.4 g) was converted to the dihydrochloride salt and recrystallization from hot methanolether afforded the analytical sample, 2.2 g of α-[3-(dimethylamino)propyl]-α-[2-(2-hydroxyphenyl)ethyl]-1-methyl-4-piperidinemethanol, hydrochloride (1:2) m.p. 205°–208° C.

Anal. Calc'd. for $C_{20}H_{34}N_2O_2 \cdot 2HCl$: C, 57.69; H, 8.6; N, 6.73; Cl, 17.02. Found: C, 57.48; H, 8.93; N, 7.07; Cl, 17.14. (c) 3,4-Dihydro-N,N-dimethyl-2-(1-methyl-4-piperidinyl)-2H-1-benzopyran-2-propanamine, hydrochloride (1:2).

A sample of α-[3-(Dimethylamino)propyl]-α-[2-(2-hydroxyphenyl)ethyl]-1-methyl-4-piperidinemethanol, hydrochloride (1:2) (4,3 g, 0.013 moles free base) in 150 ml concentrated hydrochloric acid is heated on the steam cone for 3 hours. Water is added, the solution basified with 10% sodium hydroxide, and extracted with dichloromethane. The organics are dried and evaporated to yield 3.3 g (81%) cyclized compound.

The dihydrochloride salt is prepared and recrystallization from methanol-ethyl acetate afforded the analytical sample 2.8 g (66%) of 3,4-dihydro-N,N-dimethyl-2-(1-methyl-4-piperidinyl)-2H-1-benzopyran-2-propanamine, hydrochloride (1:2) mp 178°–180° C.

Anal. Calc'd. for $C_{20}H_{32}N_2O \cdot 2HCl \cdot 0.66\ H_2O$: C, 59.85; H, 8.92; N, 6.98; Cl, 17.66. Found: C, 60.01; H, 9.23; N, 6.77; Cl, 17.84.

EXAMPLE 3A

Grignard reagent of 4-chloro-N-methylpiperidine

The free base (formed by treatment in dilute NaOH) from 4-chloro-N-methylpiperidine hydrochloride (60 g) is converted to the grignard with magnesium (0.38 g-atom) in 1 liter of a 1:1 tetrahydrofuran: ether mixture.

EXAMPLE 4

3,4-Dihydro-2-methyl-2-(1-methyl-4-piperidinyl)-2H-1-benzopyran-6-ol, acetate ester, hydrochloride (1:1)

A mixture of 300 g (1.8 moles) 2,5-dimethoxybenzaldehyde, 500 ml of acetone and 200 ml of water is treated over 20 min with 50 ml of 10% sodium hydroxide with cooling to 25°–31° C. Stirring at 25° C. is continued for 2½ hours, then the mixture is acidified with 10% HCl and stirred 1 hour. The layers are separated and the aqueous extracted with benzene. The combined organics are washed with 1:1 water:saturated salt (emulsion broken by heating on a steam cone), the organics concentrated at 1 atm. on the steam cone and finally a heating mantle. Distillation in vacuo gives 270 g (75%), bp 105°–108° C., at 0.5 mm Hg. The entire sample in 700 ml of ethyl acetate and 2 g of platinum oxide is reduced by $H_2$ at 40 psi for 1.5 hours, when uptake ceased. Filtration and evaporation gives the oily ketone.

The Grignard reagent from 0.15 mole of N-methyl-4-chloropiperidine hydrochloride and 0.2 mole of magnesium is prepared in tetrahydrofuran (THF) by the procedure of Example 3A. The THF is replaced with benzene by distilling out the THF in the presence of benzene, and the cooled slurry in 300 ml of benzene treated with 20.8 g of ketone (0.1 mole) in 100 ml of benzene. The mixture is refluxed 2 hours, cooled and treated with ammonium chloride solution. The organics are dried (potassium carbonate) and evaporated to 40 g of oil. Acid-base treatment gives 7 g (23%) crude adduct with no carbonyl in the infra red spectrum.

The diether (7 g, 0.023 moles) is refluxed under nitrogen for 2 hours with 100 ml of 48 HBr. Diluted with 1 liter of water and basified with 10% sodium hydroxide. Carbon dioxide is bubbled in to give a grey solid. This is filtered and the filtrates extracted with chloroform. The extracts are dried (magnesium sulfate) and evaporated to an oil. This is triturated with ether and the filtrates evaporated and acetylated by heating for 2 hours with acetic anhydride and then evaporating to an oil which is washed with chloroform and bicarbonate. Drying (magnesium sulfate) gives material with one polar and one nonpolar spot on thin layer chromatography. The solution is passed through a pad of neutral alumina, activity II, to remove the polar spot, and evaporated to an oil which was partitioned into hexane soluble and insoluble fractions. The hexane soluble (1.5 g) is taken up in 100 ml of ethyl acetate, converted to the hydrochloride with HCl in isopropanol, and treated with ether to the cloud point. White crystals form. More ether is added, and filtration gives the solid acetate hydrochloride, 0.9 g (12%) 3,4-dihydro-2-methyl-2-(1-methyl-4-piperidinyl)-2H-1-benzopyran-6-ol, acetate ester, hydrochloride (1:1) mp 206°–208° C.

Anal. Calc'd. for $C_{18}H_{25}NO_3.HCl$: C, 63.62; H, 7.71; N, 4.12; Cl, 10.43. Found: C, 63.47; H, 7.95; N, 4.02; Cl, 10.67.

EXAMPLE 4A 3,4-Dihydro-2-methyl-2-(1-methyl-4-piperidinyl)-2H-1-benzopyran-6-ol, hydrochloride (1:1)

A 3 g sample of crude, 3,4-dihydro-2-methyl-2-(1-methyl-4-piperidinyl)-2H-1-benzopyran-6-ol, acetate ester, hydrochloride (1:1) prepared in Example 4 (0.009 moles) is added to 100 ml of methanol, 2 ml of HCl in isopropanol added, and the mixture refluxed for one-half hour. Evaporation gives a brown solid. This is slurried in a small amount of methanol and filtered to give a white solid, 2.1 g (80%).

The white solid is recrystallized from 20 ml of methanol to give 1.5 g of 3,4-dihydro-2-methyl-2-(1-methyl-4-piperidinyl)-2H-1-benzopyran-6-ol, hydrochloride (1:1) mp 280°–281° C.

Anal. Calc'd. for $C_{16}H_{23}NO_2.HCl$: C, 64.53; H, 8.13; N, 4.70; Cl, 11.91. Found: C, 64.57; H, 8.40; N, 4.63; Cl, 11.67.

EXAMPLE 5

2-[3-Dimethylamino)propyl]-3,4-dihydro-2-methyl-2H-1-benzopyran-6-ol, hydrochloride (1:1)

The free base from 64 g of dimethylaminopropylchloride hydrochloride (42 g, 0.35 moles) is converted to the grignard with 9.0 g of magnesium (0.38 g-atom) in 1 liter of a 1:1 tetrahydrofuran:ether mixture. To this is added 45 g (0.22 moles) of 4-(2,5-dimethoxyphenyl)-2-butanone in ether at room temperature, then the mixture is refluxed for two hours, cooled, and treated with excess aqueous ammonium chloride. The organic layer is dried (potassium carbonate) evaporated to an oil, and the oil taken through acid-base treatment to give 57 g (88%) of yellow oil containing no ketone.

A solution of 54 g (0.18 moles) of grignard adduct in 400 ml of acetic acid and 200 ml of 48% HBr is refluxed for 3.5 hours, then stripped to dryness and taken up in 200 ml of acetic anhydride. After standing 2 days the mixture if evaporated to an oil, then shaken with chloroform and aqueous bicarbonate. The dried (magnesium sulfate) organics are passed through 200 g of neutral activity III alumina and evaporated to give 15.0 g (29%) crude acetate. Two more passes through neutral III alumina did not remove polar spot in TLC. The polar material from one pass is eluted with 5% methanol and converted to the same hydrochloride obtained when 1.5 g of the acetate is refluxed in methanolic HCl for 0.5 hour, evaporated to a solid and crystallized from ethyl acetate:acetonitrile to give 1.1 g (75%) of the chromanol hydrochloride.

The combined solids (2.4 g) are dissolved in methanol: acetonitrile, treated with Darco, and boiled down to 50 ml of acetonitrile, to give on cooling and scratching, 2.1 g 2-[3-(Dimethylamino)propyl]-3,4-dihydro-2-methyl-2H-1-benzopyran-6-ol, hydrochloride (1:1) mp 182°–184° C.

Anal. Calc'd. for $C_{15}H_{23}NO_2.HCl$: C, 63.04; H, 8.47; N, 4.90; Cl, 12.41. Found: C, 62.74; H, 8.34; N, 5.06; Cl, 12.25.

EXAMPLE 6

4-(3,4-Dihydro-2-methyl-2H-benzopyran-2-yl)-1-methylpiperidine, hydrochloride, hydrate (1:1:1)

o-Anisalacetone is prepared by adding 70 ml of 10% aqueous sodium hydroxide to 7.7 moles of acetone, 280 ml of water, and 2.8 moles of o-anisaldehyde, slowly with cooling to maintain the temperature in the range of 25°–31° C. Another 2 hours stirring followed by acidification, separation of layers, dehydration with acid in benzene at reflux, and finally distillation at reduced pressure gives the crude o-anisalacetone.

The crude o-anisalacetone is hydrogenated (100 g/l liter of ethyl acetate and 1 g of platinum oxide) and then distilled to give 1.25 moles (45%) of 1-(o-methoxyphenyl)-3-butanone, bp 90°–110° C., 0.15 mm Hg.

The Grignard reagent from 40 g of N-methyl-4-chloropiperidine hydrochloride is prepared in 200 ml of tetrahydrofuran (THF). To this at reflux is added 21 g (0.12 mole) of the butanone, the mixture refluxed an additional ¼ hour, then cooled in ice and treated with 300 ml of saturated ammonium chloride. The layers are separated, and the aqueous reextracted with THF. Drying (potassium carbonate) and evaporation gives an oil which is taken up in hexane and extracted with 5% HCl. The aqueous is washed with hexane, then basified with 10% sodium hydroxide, extracted with dichloromethane, dried over carbonate and evaporated to 14 g (43%) of crude product.

The crude Grignard adduct (11 g, 0.04 mole) is refluxed for 3 hours in 200 ml of 48% HBr. The dark mixture is diluted with water and basified with 10% sodium hydroxide, extracted with dichloromethane, dried over carbonate and evaporated to 8 g of oil. Filtration through a column of Activity I, neutral alumina in dichloromethane gives 3 g (30%) of colorless oil. This is converted to the hydrochloride in isopropanol from which it crystallized. Recrystallization from ethanol-ether and then from methanol-ether gives 1.4 g of highly crystalline anhydrous salt which on exposure to moist air picked up one mole of water to give 4-(3,4-dihydro-2-methyl-2H-benzopyran-2-yl)-1-methylpiperidine, hydrochloride, hydrate (1:1:1).

Anal. Calc'd. for $C_{16}H_{23}NO\cdot HCl\cdot H_2O$: C, 64.09; H, 8.74; N, 4.67; Cl, 11.82. Found: C, 64.05; H, 8.59; N, 4.57; Cl, 11.95.

EXAMPLE 7

2-[3-(Dimethylamino)propyl]-3,4-dihydro-2-phenyl-2H-1-benzopyran-6-ol, hydrochloride (1:1)

(a)

α-[3-(Dimethylamino)propyl]-2,5-dimethoxy-α-phenyl-benzenepropanol, hydrochloride (1:1)

To a cooled solution of 12.7 g (0.32 mole) of sodium hydroxide in 72 ml of 95% ethanol and 114 ml of water is added 42 g (0.25 mole) of 2,5-dimethoxybenzaldehyde, and then 30 ml (0.25 mole) of acetophenone (at a temperature less than or equal to 20° C.). The mixture is stirred at 25° C. for 6 hours, then stored at ambient temperature for 2.5 days. At this time, water is added and the resulting oil extracted into ether. Drying (magnesium sulfate) and evaporation gives 69 g of crude oil.

The crude oil is dissolved in 1 liter of ethyl acetate and hydrogenated over 0.5 platinum oxide at 46 psi. After 1 equivalent of hydrogen has been absorbed the uptake ceases. The catalyst is filtered and solvent evaporated to give crude saturated ketone.

A 10 g sample of crude ketone is reacted in tetrahydrofuran at 0° C. with the Grignard prepared from 5 g of magnesium and the entire quantity of free base liberated from 20 g of dimethylaminopropylchloride hydrochloride. The mixture is allowed to come to room temperature overnight, refluxed for 3 hours, then cooled in ice and treated with excess water. The aqueous slurry is separated and re-extracted with THF. The organics are dried (carbonate) and evaporated to 15 g of oil showing no carbonyl in their spectrum. A minor polar impurity is removed by chromatography on 200 g of neutral II alumina in chloroform, to give 11.5 g of homogeneous adduct as an oil.

A 1.5 g sample of the Grignard adduct is converted to the hydrochloride in ether with HCl in isopropanol to give a gum which solidified on trituration with ether. This solid, 0.8 g, mp 150°–154° C. is dissolved in 80 ml of hot acetonitrile, filtered, and diluted with ether until cloudy. Standing for 3 days and filtering gives 0.7 g α-[3-(dimethylamino)propyl]-2,5-dimethoxy-α-phenyl-benzenepropanol, hydrochloride (1:1) mp 180°–183° C.

Anal. Calc'd. for $C_{22}H_{31}NO_3\cdot HCl$: C, 67.07; H, 8.19; N, 3.56; Cl, 9:00. Found: C, 66.95; H, 8.45; N, 3.69; Cl, 9.25.

(b)

2-[3-(Dimethylamino)propyl]-3,4-dihydro-2-phenyl-2H-1-benzopyran-6-ol, hydrochloride (1:1)

A 10 g sample of the free base of α-[3-(Dimethylamino)propyl]-2,5-dimethoxy-α-phenyl-benzenepropanol, hydrochloride (1:1) (0.028 mole) is refluxed for 3 hours in 50 ml of 48% HBr and 100 ml of glacial acetic acid, then evaporated to an oil. This is then dissolved in 75 ml of acetic anhydride and then stripped after 4 hours at 25° C. The oil is partitioned between water and ether, the aqueous separated and treated with excess bicarbonate. Extracting with chloroform drying (magnesium sulfate) and evaporation give 12 g of oil. This is triturated with ether and the filtrate converted to hydrochloride with HCl in isopropanol. The resulting gum is dissolved in acetontrile, decolorized with DARCO (Trademark), and diluted with ether to give dark oils. The supernatant is evaporated and then dissolved in ethyl acetate and diluted with ether to give 3 g of solid above a partially solidified oil. The oil is triturated with ethyl acetate to give 1.5 g solid for a total yield of 41% of acetate hydrochloride.

The salt (3.5 g, 9 mmoles) is hydrolyzed in methanolic HCl on the steam bath. Stripping gives an oil which crystallized in acetone. Recrystallization from acetonitrile gives 1.0 g of 2-[3-(dimethylamino)propyl]-3,4-dihydro-2-phenyl-2H-1-benzopyran-6-ol, hydrochloride (1:1) mp 192°–195° C.

Anal. Calc'd. for $C_{20}H_{25}NO_2\cdot HCl$: C, 69.05; H, 7.53; N, 4.03; Cl, 10.19. Found: C, 68.85; H, 7.68; N, 4.01; Cl, 10.04.

EXAMPLE 8

2-[3-(Dimethylamino)propyl]-3,4-dihydro-2-methyl-2H-1-benzopyran-8-ol, acetate ester, hydrobromide (1:1)

A mixture of 2,3-dimethoxybenzaldehyde (150 g, 0.9 moles), 250 ml of acetone, and 100 ml of water is maintained at 25°–35° C. while 25 ml of 10% sodium hydroxide is added over 15 minutes. Following the base addition, the mixture is stirred at 25° C. for 2½ hours, then acidified with 10% sulfuric acid. The mixture is extracted with benzene, the organics dried over magnesium sulfate, and distilled, giving 120 g (68%), bp 143°–148° C. at 0.2 mm Hg. Two higher boiling fractions are obtained (20 g) with identical IR spectra to the major fraction for a total yield of 79%.

The 120 g fraction is reduced in 1 liter of ethyl acetate over 1 g of platinum oxide, at room temperature. Evaporation gives the dihydro ketone. The Grignard reagent from 24 g of dimethylaminopropyl chloride (free base, 0.2 moles) and 5 g of magnesium is prepared in 250 ml of tetrahydrofuran (THF). The ketone (40 g, 0.2 moles) is added to the Grignard at 0° C., then the mixture is refluxed for 3 hours. The mixture is then cooled, treated with excess saturated ammonium chloride, and the THF layer evaporated to an oil.

Acid-base treatment of the product in ether gives 35 g (61%) of ketone-free adduct.

The Grignard product (35 g, 0.12 moles) is refluxed for 4 hours in a mixture of 300 ml of glacial acetic acid and 150 ml of 48% HBr. The mixture is evaporated to an oil, then taken up in 200 ml of acetic anhydride, stood for 5 hours at 25° C., then evaporated to an oil. This is taken up in acetonitrile, then diluted with ethyl acetate and finally ether to give 28 g (68%) of the hydrobromide salt.

A 5 g sample is recrystallized from acetonitrile-ethyl acetate-ether to give 1.8 g of white 2-[3-(dimethylamino)propyl]-3,4-dihydro-2-methyl-2H-1-benzopyran-8-ol, acetate ester, hydrobromide (1:1), mp 127°–133° C.

Anal. Calc'd. for $C_{17}H_{25}NO_3 \cdot HBr$: C, 54.84; H, 7.04; N, 3.76; Br, 21.46. Found: C, 54.71; H, 7.26; N, 3.60; Br, 21.41.

EXAMPLE 9

2-[3-(Dimethylamino)propyl]-3,4-dihydro-2-methyl-2H-1-benzopyran-8-ol, hydrobromide (1:1)

4 g of recrystallized 2-[3-(dimethylamino)propyl]-3,4-dihydro-2-methyl-2H-1-benzopyran-8-ol, acetate ester, hydrobromide (1:1), the product of Example 8, (0.012 moles) in 100 ml of methanol is treated with 1 ml of 48% HBr and refluxed for 1 hour. The solvent is evaporated and the resulting oil dissolved in 50 ml of acetontrile and 50 ml of ethyl acetate. This is treated with DARCO (Trademark) then diluted to 250 ml with ether to give an off-white solid. Recrystallization in the same manner gives 1.7 g (47%) of 2-[3-(dimethylamino)propyl]-3,4-dihydro-2-methyl-2H-1-benzopyran-8-ol, hydrobromide (1:1), mp 132°–135° C.

Anal. Calc'd for $C_{15}H_{23}NO_2 \cdot HBr$; C, 54.55; H, 7.32; N, 4.24; Br, 24.20. Found: C, 54.79; H, 7.44; N, 4.17; Br, 23.95.

EXAMPLE 10

3,4-Dihydro-N,N-dimethyl-2-phenyl-2H-1-benzopyran-2-propanamine, hydrochloride (1:1)

(a)

α-[3-(Dimethylamino)propyl]-2-hydroxy-α-phenylbenzenepropanol, hydrochloride (1:1)

Following a literature procedure (Ber. 29, 378 (1896), a 50 g (0.41 mole) sample of salicylaldehyde is dissolved in 140 ml of 10% sodium hydroxide and then treated simultaneously over 15 minutes with 200 ml of 10% sodium hydroxide and a solution of 50 g (0.42 mole) acetophenone in 100 ml of 95% ethanol. After the addition the mixture is diluted to 2 liters with ethanol and enough water to bring the mixture almost to the cloud point. The dark red homogeneous mixture is stored for 8 days at 25° C., then acidified with 6 N sulfuric acid. The aqueous phase is decanted from the resulting sticky brown mass. The sticky solid is triturated with benzene to give a bright yellow solid. This is filtered and washed with benzene until the washes were colorless. Air drying gives 44 g crude product. Recrystallization from benzene gives 30 g (33%) of dry crystalline yellow solid, a chalcone.

The crystalline chalcone is slurried with 200 ml of ethyl acetate, 1 g of platinum oxide added, and the mixture hydrogenated at 40 psi. After 1.5 times the theoretical amount of hydrogen is taken up, the catalyst is filtered and the solution evaporated. The resulting oil is chromatographed on 600 g of neutral II alumina in chloroform to give 20 g (66%) of white crystalline solid on evaporation of the first 3 liters of solvent.

A solution of 8 g (0.066 moles) of dry dimethylaminopropyl chloride in 200 ml of tetrahydrofuran (THF) is converted to the grignard with 3 g of magnesium. After one half hour of reflux subsequent to grignard formation, the mixture is cooled to 25° C., and the ketone (7.5 g, 0.033 moles) in 80 ml of tetrahydrofuran is added over a half hour. The mixture is stirred overnight at 25° C., then refluxed for 2 hours, cooled, and treated with saturated ammonium chloride. The aqueous layer is reextracted with chloroform, and the combined organics dried (potassium carbonate), benzene added, and evaporated to an oil containing some ketone. This is dissolved in 300 ml of ether, filtered, and treated with excess HCl in ether-isopropanol. The solid is washed with ether and dried in vacuo to give 6 g (52%) solid hydrochloride.

A 2 g sample of hydrochloride is taken up in 30 ml of acetontrile and 30 ml of dichloromethane, diluted with 100 ml of ethyl acetate and finally ether to the cloud point, to give 1.1 g of white solid, α-[3-(dimethylamino)propyl]-2-hydroxy-α-phenylbenzenepropanol, hydrochloride (1:1), mp 145°–148° C.

Anal. Calcd. for $C_{20}H_{27}NO_2 \cdot HCl$: C, 68.65; H, 8.07; N, 4.00; Cl, 10.13. Found: C, 68.65; H, 7.93; N, 4.02; Cl, 10.00.

(b)

3,4-Dihydro-N,N-dimethyl-2-phenyl-2H-1-benzopyran-2-propanamine, hydrochloride (1:1)

A sample of crude α-[3-(dimethylamino)propyl]-2-hydroxy-α-phenylbenzenepropanol, hydrochloride (1:1) (2 g, 0.017 mmoles) is heated in 100 ml of dilute HCl at 100° C. for 2 hours, cooled and extracted with ether. The aqueous is basified with 10% sodium hydroxide and extracted 4 times with chloroform. The organics are dried (carbonate) and evaporated to 1.8 g of oil which partially crystallized on standing. This is taken up in ether and converted to the hydrochloride which oiled out. Trituration with ethyl acetate gives 0.6 g of white solid (32%). This is recrystallized by dissolving in dichlorométhane, adding 30 ml of ethyl acetate, and boiling down to 20 ml. Standing at 25° C. gives, after drying at 80° C., 0.4 g, 3,4-dihydro-N,N-dimethyl-2-phenyl-2H-1-benzopyran-2-propanamine, hydrochloride (1:1) mp 126°–128° C.

Anal. Calc'd. for $C_{20}H_{25}NO \cdot HCl$: C, 72.38; H, 7.90; N, 4.22; Cl, 10.68. Found: C, 72.41; H, 8.20; N, 4.16; Cl, 10.61.

EXAMPLE 11

4-(3,4-Dihydro-2-methyl-2H-1-benzopyran-2-yl)-1-nonylpiperazine, hydrochloride (1:1)

The free base 4-(3,4-dihydro-2-methyl-2H-benzopyran-2-yl)-1-methylpiperidine, hydrochloride, hydrate (1:1:1) the product of Example 6 (10.0 g, 0.04 mole) is dissolved in 150 ml of toluene at 5° C. Trichloroethylchloroformate (14.3 g, 0.07 mole) is added dropwise. After addition, the reaction mixture is heated at reflux for 6 hours. After standing overnight at room temperature, the toluene solution is washed sequentially with 10% NaOH, $H_2O$, 10% HCl, and $H_2O$. The toluene then is dried with $MgSO_4$, filtered and concentrated in vacuo to yield 18.4 g of crude material which is used in the following reduction.

The above crude product is dissolved in 175 ml. of glacial acetic acid. Zinc dust (20.0 g) is added portionwise at room temperature. After addition the reaction mixture is stirred for 5 hours. It is then filtered and the filtrate is concentrated in vacuo. The pot residue is dissolved in water and washed with ether. The aqueous solution is made basic with 10% NaOH and digested on the steam cone for 30 minutes. It is then cooled and product is extracted with chloroform. The chloroform is dried with MgSO₄, filtered and conc. in vacuo to yield 5.2 g of secondary amine product.

The above secondary amine product (5.2 g) is dissolved in 50 ml of pyridine and the solution is cooled to 5° C. Nonanoyl chloride (4.2 g) is dissolved in 20 ml of toluene and is added dropwise to the pyridine solution. After addition it is stored at 5° C. for 2 days. The solution is concentrated in vacuo and the pot residue is dissolved in ether and washed sequentially with 5% HCl, 5% NaOH then twice with water. The ether is dried with MgSO₄, filtered and concentrated in vacuo to yield 5.8 g of very viscous oil.

The above viscous oil is dissolved in 75 ml of anhydrous tetrahydrofuran and cooled to 5° C. Diborane (32 ml of 1 molar tetrahydrofuran solution) is added dropwise under nitrogen. After addition the reaction mixture is heated at reflux for 2 hours and allowed to stand at room temperature over-night. The solution is cooled to 5° C. and 60 ml of 6 N HCl is added dropwise. After addition the tetrahydrofuran is distilled at atmospheric pressure. The acidic aqueous solution is neutralized with 10% NaOH and product is extracted with ether. The ether is dried with MgSO₄, filtered and concentrated in vacuo. The hydrochloride salt is prepared in isopropanol-HCl. Product crystallized slowly, it is filtered and recrystallized from ethyl acetate to yield 3.4 g.

It is then recrystallized from acetone with 5% ethanol. Yield of analytical sample 1.4 g 4-(3,4-dihydro-2-methyl-2H-1-benzopyran-2-yl-1-nonylpiperazine, hydrochloride (1:1) mp 212°–220° C.

Calc. for $C_{24}H_{39}NO \cdot HCl$: C, 73.16; H, 10.23; N, 3.55; Cl, 9.00. Found: C, 72.93; H, 9.99; N, 3.33; Cl, 9.01.

EXAMPLE 12

3,4-Dihydro-N,2-dimethyl-N-nonyl-2H-1-benzopyran-2-propanamine, barbituric acid salt (1:2)

A 115 g sample of dimethylaminopropylchloride hydrochloride is converted to 89 g (0.74 mol) of free base (NaOH solution, pentane extraction, MgSO₄ drying). This is converted to the grignard with 17 g (0.71 g atom) of magnesium in 1 l of tetrahydrofuran. To this is added 72 g (0.4 mole) of 4-(2-methoxyphenyl)-butan-2-one (as prepared in Example 6) in 500 ml of tetrahydrofuran with cooling. After refluxing 2 hours the reaction is cooled and treated with aqueous NH₄Cl. The organic layer is separated and combined with the additional ether extracts. Drying (Na₂SO₄) and evaporation gives 89 g (83%) of oil. The crude adduct (89 g, 0.34 mole) is taken up in 1 l of glacial acetic acid and 300 ml of 48% HBr and refluxed overnight. The mixture is then stripped to an oil and basified, extracted with ether, dried (K₂CO₃), and evaporated to an oil. This is distilled at 1 mm Hg to give the benzopyran 36 g (46%), bp 105°–115° C.

A 24 g (0.1 mole) sample of the distilled benzopyran in 250 ml of toluene is cooled in an ice bath and treated with 30 g (0.14 mole) of trichloroethylchloroformate by drops. The mixture is stirred at 0° for 1 hour then refluxed under N₂ overnight. The reaction mixture is cooled and shaken thoroughly with 10% NaOH, then with dilute HCl, and finally H₂O. The organics are dried (MgSO₄) and evaporated to an oil. This is taken up in 100 ml of acetic acid and treated with 20 g of powdered zinc in portions. The mixture is stirred at 35°–40° for 5 hours, filtered and evaporated. The residue is basified strongly with 10% NaOH and heated for 3 hours on a steam cone. Cooling, ether extraction, drying (K₂CO₃) and evaporation gives an oil. This is taken up in ether and converted to the salt with HCl in isopropanol. Trituration of the resulting oil with ethyl acetate and ether gives 19.4 g (76%) of white hydrochloride of the secondary amine in two crops.

A 27.4 g sample of the above hydrochloride is converted to 23.5 g (0.107 mole) of free base. This is dissolved in 250 ml of pyridine and treated at 0° with 20 g (0.114 mole) of nonanoyl chloride in 20 ml of toluene. After the mixture stands at 25° C. overnight and is evaporated to a slurry, water, ether and dilute NaOH are added, the organics separated and extracted with 3 N H₂SO₄. The organic layer is washed with water, dried (MgSO₄) and evaporated to 29.8 g (77%) of oily amide.

The crude amide (29.8 g, 0.083 mole) is cooled in 400 ml tetrahydrofuran at 0° and treated with 175 ml of 1 M BH₃ in tetrahydrofuran, refluxed for 3 hours, then cooled to 25° C. overnight. To this mixture is added 200 ml of 10% HCl (cautiously). The tetrahydrofuran is distilled off, until the bp reached 100° C. The resulting mixture is cooled and basified with 10% NaOH, extracted with ether, dried (Na₂CO₃) and evaporated. Benzene is added and evaporated to give an oil, 27.7 g (97%).

A 1.4 g (4 mmole) sample of the crude diborane reduction product is dissolved with 0.9 g (7 mmole) of barbituric acid in 150 ml of methanol. The solution is evaporated to a solid which on trituration with ether gives 2.2 g of solid. Recrystallization from methanol acetonitrile gives 1.5 g (71%) of light yellow solid, 3,4-dihydro-N,2-dimethyl-N-nonyl-2H-1-benzopyran-2-propanamine, barbituric acid salt (1:2) mp 177°–180° C.

Analysis calc'd. for $C_{23}H_{39}NO_2 \cdot O_3$: C, 61.87; E, 7.87; N, 11.64. Found: C, 61.60; H, 7.61; N, 11.48.

EXAMPLE 13

6-Amino-3,4-dihydro-N,2-dimethyl-N-nonyl-2H-1-benzopyran-2-propanamine, hydrochloride (1:2)

22.2 g (0.064 mole) of 3,4-dihydro-N,2-dimethyl-N-nonyl-2H-1-benzopyran-2-propanamine, barbituric acid salt (1:2), the product of Example 12, (free base) in 150 ml of acetic anhydride is treated with 2 ml of concentrated H₂SO₄ then cooled to −20° C. in an ice-acetone bath. A solution of 6.5 ml of conc. HNO₃ in 150 ml of acetic anhydride is prepared with cooling, and then added over ½ hour to the cold amine solution. The reaction mixture is stored in the freezer for 2½ days, then diluted with 300 ml of methanol. With ice cooling to maintain T<40° C., portions of 10% NaOH are added until no temperature rise is noted on further addition, and the pH is 14. Dilution with water, chloroform extraction, drying (Na₂SO₄) and evaporation gives 25 g of crude nitro compound. This material displays three non-polar components by Tlc on alumina (etherhexane, 1:1). Careful chromatography of a sample of the crude product on neutral alumina, activity III gives the starting material (minor component) as the least polar spot, the 6-nitro derivative of intermediate polarity, and the 8-nitro compound as the most polar. These assignments are made by NMR. Chromatography of the remaining material gives a total of 1.5 g starting material, 2.5 g reasonably pure 6-nitro compound, and 9.5 g of a mixture of 6- and 8-nitro compounds, for a total of 12 g of mono-nitrated materials (48%).

The 2.5 g sample of 6-nitro derivative is reduced by treating a solution of the compound in 10 ml of concentrated HCl and 5 ml of absolute ethanol with 7.5 g of stannous chloride dihydrate in 10 ml of absolute ethanol and heating on a steam cone for 1 hour. The mixture is diluted with 10% NaOH, extracted with ether, dried ($Na_2SO_4$) and evaporated, benzene added, and evaporated again. The oil in ethyl acetate are converted to the hydrochloride with HCl in isopropanol. This gives a gum which crystallizes when a small amount of methanol is added. When the 9.5 g sample is reduced in the same fashion using 42 ml of concentrated HCl and 21 ml of absolute ethanol with the addition of 34 g of stannous chloride dihydrate in 45 ml of alcohol, followed by conversion to the hydrochloride, the crystalline 6-amino dihydrochloride comes out of solution whereas the other isomer stays in the mother liquors. The two samples of hydrochloride are identical by IR as well as TlC of their free bases. The mother liquor of the 9.5 g preparation gives a compound which is less polar than the 6-amino compound, but which showed no nitroabsorption in the IR spectrum, and this presumably is the 8-amino derivative. The combined hydrochloride solids are recrystallized from ethyl acetate-methanol to give 5.8 g (43%). Another recrystallization gives solid 6-amino-3,4-dihydro-N,2-dimethyl-N-nonyl-2H-1-benzopyran-2-propanamine, hydrochloride (1:2) mp 165°–169° C. which analyzes for the presence of ½ mole of water of hydration.

Analysis calc'd. for $C_{23}H_{40}N_2O.2HCl·½H_2O$: C, 62.42; H, 9.79; N, 6.33; Cl, 16.02. Found: C, 62.47; H, 9.64; N, 6.10; Cl, 16.11.

EXAMPLE 13 A

6-N-acyl-3,4-dihydro-N,2-dimethyl-N-nonyl-2H-1-benzopyran-2-propanamine, hydrochloride (1:2)

6-Amino-3,4-dihydro-N,2-dimethyl-N-nonyl-2H-1-benzopyran-2-propanamine, hydrochloride (1:2) is dissolved in pyridine and treated with one equivalent of an acyl chloride at 0° C. After 24 hours at 0° the mixture is evaporated in vacuo, taken up with water and ether. The organics are washed with bicarbonate, dried ($Na_2SO_4$) and evaporated to the solid 6-N-acyl-3,4-dihydro-N,2-dimethyl-N-nonyl-2H-1-benzopyran-2-propanamine, hydrochloride (1:2).

EXAMPLE 14

2-[(3,4-Dihydro-2-methyl-2H-1-benzopyran-2-yl)-methyl]-1-nonylpiperidine, barbituric acid salt (1:2)

6 g (0.024 mole) of 2-[(3,4-dihydro-2-methyl-2H-benzopyran-2-yl)-methyl]piperidine, oxalate salt (2:1), the product of Example 1, (free base) in 70 ml of pyridine at 0° C. is treated with 4.5 g (0.026 mole) of nonanoyl chloride and allowed to warm to 25° C. overnight. The solvent is stripped off and the residue taken up in water and ether. Washing with dilute $H_2SO_4$, drying ($Na_2SO_4$) and evaporation gives 7.8 g (84%) of oily amide.

The amide (7.8 g, 0.02 moles) in 100 ml of tetrahydrofuran (THF) is treated with 40 ml of 1 M $BH_3$ in tetrahydrofuran at 0° C. The mixture is stirred without cooling for 2 hours, then refluxed for 2 hours. The mixture is then cooled and treated cautiously with an equal volume of 10% HCl. This mixture is distilled until the bp is 100° C., then cooled and the oily hydrochloride extracted into chloroform. The extract is shaken with dilute $NH_4OH$, dried ($Na_2SO_4$) and evaporated to 6.8 g of an oil. A 2.7 g sample of oil is dissolved with 1.63 g of barbituric acid in methanol, filtered, and evaporated to a foam. Trituration with ether gives 3.9 g (90% from amide) of barbiturate salt. Recrystallization from ethyl acetate gives 2.5 g, 2-[(3,4-dihydro-2-methyl-2H-1-benzopyran-2-yl)-methyl]1-nonylpiperidine, barbituric acid salt (1:2) mp 80°–100° C., which analyzes for the presence of ½ mole of water.

Analysis calc'd. for $C_{25}H_{41}NO.2C_4H_4N_2O_3·½H_2O$: C, 62.24; H, 7.91; N, 10.99. Found: C, 62.29; H, 7.53; N, 10.76.

EXAMPLE 15

3,4-Dihydro-2-methyl-2-[(methylnonylamino)-propyl]-2H-1-benzopyran-6-ol, barbituric acid salt (1:2)

1.1 g (2.5 mmole) of 6-amino-3,4-dihydro-N,2-dimethyl-N-nonyl-2H-1-benzopyran-2-propanamine, hydrochloride (1:2), the product of Example 13, is shaken with aqueous bicarbonate and ether, the organics dried and evaporated to an oil. The residue is taken up in 20 ml of 3 N $H_2SO_4$, cooled in an ice bath and treated with 0.17 g (2.5 mmole) of sodium nitrite in 2 ml of water, under $N_2$. The mixture is stirred at 0° C. for 20 minutes, then added slowly to 200 ml of refluxing 2 N $H_2SO_4$. After an additional ½ hour of reflux, the mixture is cooled and basified with ammonium hydroxide, extracted with chloroform, dried ($MgSO_4$) and evaporated to a rapidly darkening oil. This is taken up in methanol and treated with 0.64 g (5 mmoles) of barbituric acid. After heating to dissolve the acid, the solution is stripped to a gum. This is partially soluble in boiling isopropanol. Decanting and cooling gives an orange solid which is filtered and dried at 50° C. over $P_2O_5$. It analyzes as the dibarbiturate, with ½ mole of water, yielding 0.5 g (32%) of 3,4-dihydro-2-methyl-2-[(methylnonylamino)-propyl]-2H-1-benzopyran-6-ol, barbituric acid salt (1:2) mp 120°–150° C.

Analysis calc'd. for $C_{23}H_{39}NO_2.2C_4H_4N_2O_3·½H_2O$: C, 59.40; H, 7.72, N, 11.17. Found: C, 59.46; H, 7.42, N, 11.54.

EXAMPLE 16

3,4-Dihydro-2-methyl-2-[(1-nonyl-2-piperidinyl)-methyl]-2H-1-benzopyran-6-ol, barbituric acid salt (1:1)

2.2 g (6.4 mmole) of 3,4-dihydro-2-methyl-2-(2-piperidinylmethyl)-2H-1-benzopyran-6-ol, hydrobromide (1:1), the product of Example 2, in 80 ml of pyridine at 0° C. is treated with 2.3 g (13.1 mmole) of nonanoyl chloride, then allowed to stand overnight at 25° C. The solvent is stripped off and the residue taken up in ether and water. The organic layer is washed with dilute $H_2SO_4$, dried ($Na_2SO_4$) and evaporated to 3.5 g of an oil. Thin layer chromatography on alumina in $CHCl_3$ showed two major components. Chromatography on neutral alumina, activity III in chloroform gives 1.3 g of ester-amide and 1.0 g of mostly amino ester, with only a weak amide absorption in the IR spectrum. This material is acylated as above to give 1.2 g of pure ester-amide for a total of 2.5 g (72%) of the oily product.

A solution of ester-amide (2.5 g, 4.6 mmoles) in 40 ml of tetrahydrofuran (THF) at 0° C. is treated with 10 m of 1 M $BH_3$ in tetrahydrofuran (THF). The mixture is warmed to 25° C. for 2 hours, refluxed for 2 hours, cooled and treated cautiously with an equal volume of 10% HCl. The mixture is distilled in 1 atm. until bp=100° C. extracted with $CHCl_3$, extracts shaken with dilute $NH_4OH$, dried ($Na_2SO_4$) and evaporated to an oil which contains some ester (by IR). This is refluxed with methanolic HCl for 2 hours, then taken to dryness. Trituration with ethyl acetate and then ethyl ether gives an oil with no carbonyl in the IR spectrum. Trituration with isopropyl ether with a trace of isopropanol gives 1.2 g of solid hydrochloride (62%) which analyzes incorrectly and does not recrystallate. This is converted to 0.7 g of oil by shaking with bicarbonate and ether, and drying and evaporating the organics. This oil (1.8 mmole) and barbituric acid (0.47 g, 3.7 mmole) is dissolved in methanol and evaporated to a foam. Trituration with ether gives 1.1 g, mp 135°–160° whose microanalysis shows greater than 3 moles of barbituric acid present per mole of base. This material is partially soluble in 60 ml of hot acetonitrile. Filtering and cooling gives 0.5 g of a heterogeneous solid, mp 187°–190° C., which analyzes for about 1.5 moles barbituric acid per mole of base. When this material is heated and stirred with 40 ml of acetonitrile and then filtered, 0.3 g (32%) of a beige solid of 3,4-dihydro-2-methyl-2-[(1-nonyl-2-piperidinyl)-methyl]-2H-1-benzopyran-6-ol, barbituric acid salt (1:1) mp 195°–203° C., is obtained which analyzes for 1 mole of barbituric acid and ½ mole of water.

Analysis calc'd. for $C_{25}H_{41}NO_2 \cdot C_4H_4N_2O_3 \cdot \frac{1}{2}H_2O$: C, 66.38; H, 8.83; N, 8.01. Found: C, 66.41; H, 8.65; N, 8.31.

EXAMPLE 17

4-(3,4-Dihydro-6-methoxy-2H-1-benzopyran-2-yl)pyridine

2-Hydroxy-5-methoxybenzaldehyde (11.6 g) and 10 ml of dimethylamine (40% aqueous) are dissolved in 100 ml of water. A scoop of 10% Pd/c is added and the reaction mixture is reduced on the Paar until the orange color disappears (68 lbs H₂ uptake on bottle gauge). The reaction mixture is filtered and the catalyst washed with ethanol. The filtrate is then concentrated to a volume of 50 ml. Product is extracted with chloroform. The chloroform is dried with MgSO₄, filtered and concentrated in vacuo to yield 13.2 g of oil. IR and NMR are consistent with desired product. (i.e. the Mannich base).

Vinyl pyridine is purified by dissolving it in ether and treating with charcoal for 2 hours. This solution is filtered through celite and concentrated in vacuo to give a light yellow oil. Vinyl pyridine (14 g) and the above Mannich base (9.6 g) are dissolved in 100 ml of mesitylene. This reaction is refluxed for 48 hours. The solution was cooled, filtered, and concentrated in vacuo. The pot residue is dissolved in ether and washed sequentially with 10% NaOH then water. The final product is extracted with 10% aqueous HCL then back neutralized with 10% NaOH. Product is re-extracted with ethyl acetate to yield 9.6 g of oil. Upon standing this oil crystallizes. It is further purified by chromatography on 100 g of neutral alumina (Act. III). Product elutes with hexane-benzene (1:1) to yield 7.0 g. By recrystallization from isopropylether-ethyl acetate (10%), 4-(3,4-dihydro-6-methoxy-2H-1-benzopyran-2-yl)-pyridine mp 88°–91° C. is obtained.

Analysis calc'd. for $C_{15}H_{15}NO_2$: C, 74.66; H, 6.27; N, 5.81. Found: C, 74.59; H, 6.12; N 5.76.

EXAMPLE 18

4-(3,4-dihydro-6-methoxy-2H-1-benzopyran-2-yl)-1,2,3,6-tetrahydro-1-methylpyridine, p-toluenesulfonate salt (1:1)

4-(3,4-dihydro-6-methoxy-2H-1-benzopyran-2-yl)-pyridine, prepared as in Example 17, is dissolved in 25 ml of acetonitrile and 4 ml of methyliodide is added dropwise. After addition the reaction mixture is heated at 35° C. for 2.5 hours then stirred at room temperature overnight. It is concentrated in vacuo and the residue is washed with ether to yield 2.9 g of crude product as a brown oil.

The above crude product is dissolved in 30 ml ethanol and 30 ml water. Sodium borohydride (3.0 g) is added portionwise. After addition the temperature is maintained at 35° C. for 1 hour. The reaction mixture then is diluted with 100 ml of water. Product is extracted with benzene and the benzene is concentrated in vacuo. This pot residue is dissolved in 20 ml 10% aqueous HCl. It is washed with ether then neutralized with 10% NaOH. Product is extracted with ether, dried with MgSO₄, filtered and concentrated in vacuo to yield 1.1 g which crystallized on standing. An analytical sample is prepared by dissolving the free base in acetonitrile along with 0.8 g of p-toluenesulfonic acid. This solution is concentrated in vacuo and recrystallized from ethyl acetate, so 4-(3,4-dihydro-6-methoxy-2H-1-benzopyran-2-yl)-1,2,3,6-tetrahydro-1-methylpyridine, p-toluenesulfonate salt (1:1) mp 134°–137° C. is obtained.

Analysis calc'd. for $C_{23}H_{29}NSO_5$: C, 64.01; H, 6.77; N, 3.25; S, 7.43. Found: C, 63.93; H, 6.90; N, 3.12; S, 7.14.

EXAMPLE 19

3,4-Dihydro-2-methyl-2-[(methylnonylamino)-propyl]-2H-1-benzopyran-8-ol, hydrochloride (1:1)

16 g (0.055 mole) of 2-[3-(dimethylamino)propyl]-3,4-dihydro-2-methyl-2H-1-benzopyran-8-ol, acetate ester, hydrobromide (1:1) (the product of Example 8) (free base) is dissolved in 300 ml of toluene cooled in ice and treated with 10.5 g (0.05 mole) of trichloroethylchloroformate by drops. After stirring 1 hour at 25° C. the mixture is heated at reflux for 5 hours, cooled and shaken with dilute HCl and saturated bicarbonate, dried (Na₂SO₄) and evaporated to an oil. This is dissolved in 300 ml of acetic acid and heated to 60° C. A 15 g portion of zinc is added and the mixture refluxed for 20 minutes. Another 15 g of zinc is added, refluxing for ½ hour, then finally 10 g of zinc is added. After a final reflux for 20 minutes, the mixture is cooled and filtered. The solution is evaporated and the residue shaken with water and ethyl acetate. The aqueous is treated with excess bicarbonate and extracted with chloroform. Drying (Na₂SO₄) and evaporation give 16.2 g of oily secondary amine. The entire sample in 200 ml of pyridine is cooled and treated with 10.3 g (0.058 mole) of nonanoyl chloride. After coming to 25° C. overnight the mixture is stripped and the residue taken up in ether and washed successively with 10% HCl and bicarbonate. Drying (Na₂SO₄) and evaporation give 20 g (96%) of oil.

This amide (0.05 mole) is dissolved in 300 ml of dry tetrahydrofuran and treated with 85 ml of 1 M BH₃ at 0° C. The mixture is then refluxed for 2 hours, cooled, and treated with excess aqueous HCl. Evaporation gives a mixture of insoluble oil and water. This is extracted with chloroform and the organics evaporated to an oil. Addition of ether gives a very small amount of dark colored oil. The ether is decanted and washed with bicarbonate, dried (Na₂SO₄) and evaporated. Tlc on silica with chloroform shows 3 spots. Chromatography on a 500 g dry silica column in chloroform separates out the least polar material. Evaporation shows it to be the borate complex of the amino ester (5 g) by IR. This is treated with excess HCl isopropanol and heated on a steam cone for 1 hour. Evaporation gives an oil which is treated with ether and allowed to stand to give 3.4 g of white solid (18%), mp 106°-112° C., which shows no borate and no acetate by IR. Two recrystallizations from acetone-ether raises the mp to 112°-116° C. One crystallization of this material from ethyl acetate afforded 1.1 g of 3,4-dihydro-2-methyl-2-[(methyl-nonylamino)-propyl]-2H-1-benzopyran-8-ol, hydrochloride (1:1) mp 132°-135° C.

Analysis Calc'd. for $C_{23}H_{39}NO_2 \cdot HCl$: C, 69.40; H, 10.13; N, 3.52; Cl, 8.91; Found: C, 69.15; H, 9.99; N, 3.80; Cl, 8.99.

EXAMPLE 20

1-[3-(Dimethylamino)propyl]-3,4-dihydro-2-phenyl-1H-1-benzopyran-6-ol, hydrochloride (1:1)

(a)

α-[3-(Dimethylamino)propyl]-2,3-dimethoxy-α-phenyl-benzenepropanol, hydrochloride (1:1)

To a cooled solution of 12.7 g (0.32 mole) of sodium hydroxide in 72 ml of 95% ethanol and 114 ml of water is added 42 g (0.25 mole) of 2,3-dimethoxybenzaldehyde, and then 30 ml (0.25 mole) of acetophenone (at a temperature less than or equal to 20° C.). The mixture is stirred at 25° C. for 6 hours, then stored at ambient temperature for 2.5 days. At this time, water is added and the resulting oil extracted into ether. Drying (magnesium sulfate) and evaporation gives 69 g of crude oil.

The crude oil is dissolved in 1 liter of ethyl acetate and hydrogenated over 0.5 platinum oxide at 46 psi. After 1 equivalent of hydrogen has been absorbed the uptake ceases. The catalyst is filtered and solvent evaporated to give crude saturated ketone.

A 10 g sample of crude ketone is reacted in tetrahydrofuran at 0° C. with the Grignard prepared from 5 g of magnesium and the entire quantity of free base liberated from 20 g of dimethylaminopropylchloride hydrochloride. The mixture is allowed to come to room temperature overnight, refluxed for 3 hours, then cooled in ice and treated with excess water. The aqueous slurry is separated and re-extracted with tetrahydrofuran. The organics are dried (carbonate) and evaporated to 15 g of oil showing no carbonyl in their spectrum. A minor polar impurity is removed by chromatography on 200 g of neutral II alumina in chloroform, to give 11.5 g of homogeneous adduct as an oil.

A 1.5 g sample of the Grignard adduct is converted to the hydrochloride in ether with HCl in isopropanol to give a gum which solidified on trituration with ether. This solid, 0.8 g, mp 150°-154° C. is dissolved in 80 ml of hot acetonitrile, filtered, and diluted with ether until cloudy. After standing for 3 days and filtering a 75% yield of homogeneous Grignard adduct is obtained after column chromatography. A 1.8 g sample of adduct yields 0.7 g of crystalline α-[3-(dimethylamino)propyl]-2,3-dimethoxy-α-phenyl-benzenepropanol, hydrochloride (1:1) mp 115°-119° C., on crystallization from acetonitrile-ether.

Analysis Calc'd. for $C_{22}H_{31}NO_3 \cdot HCl$: C, 67.07; H, 8.19; N, 3.56; Cl, 9.00. Found: C, 66.83; H, 8.27; N, 3.39; Cl, 9.02.

(b)

[3-(Dimethylamino)propyl]-3,4-dihydro-2-phenyl-2H-1-benzopyran-8-ol, acetate ester, oxalate salt (1:1)

40 g of α-[3-(dimethylamino)propyl]-2,3-dimethoxy-α-phenylbenzenepropanol, hydrochloride (1:1) is prepared from 32 g of ketone and 40 g of the dimethylaminopropyl chloride hydrochloride. This is dissolved in 500 ml of acetic acid and 250 ml of 48% HBr. The mixture is refluxed 6 hours, cooled to 25° C. overnight, then evaporated to a black oil. This is dissolved in 500 ml of acetic anhydride and 500 ml of pyridine. After standing overnight this solution is evaporated in vacuo. Addition of ethyl acetate gives a solid, pyridine hydrobromide. The filtrates are washed (NaHCO₃), dried (MgSO₄) and filtered through a pad of neutral III alumina. The organics are stripped, xylene added, and stripped again to an oil. This oil is converted to the oxalate in isopropanol. Ether is added to precipitate an oil. This is covered with ethyl acetate and gives a solid, 9.8 g (18%).

The mother liquors from the 9.8 g of oxalate are evaporated to an oil and converted to a free base. This is chromatographed on 500 g of neutral, activity III alumina, using successively ether, ethyl acetate, and chloroform. With ethyl acetate a single spot (by TLC) material is obtained which is converted to a different oxalate from the ring alkylation material. This material, 1.6 g (4%), is recrystallized from ethyl acetate to give 1.1 g [3-(dimethylamino)propyl]-3,4-dihydro-2-phenyl-2H-1-benzopyran-8-ol, acetate ester, oxalate salt (1:1) mp 106°-109° C.

Analysis calc'd. for $C_{22}H_{27}NO_3 \cdot C_2H_2O_4$: C, 65.00; H, 6.59; N, 3.16. Found: C, 64.78; H, 6.53; N, 3.06.

EXAMPLES 21 TO 62

In Examples 21–62 by following the procedure of Example 10 but substituting a compound of Column I in place of salicyladehyde and a compound of Column II in place of acetophenone and the compound of Column III in place of the grignard of dimethylaminopropyl chloride then the product of Column IV is obtained.

Column I

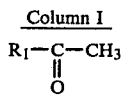

Column II

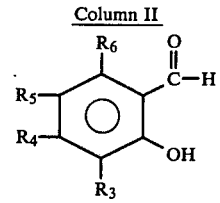

Column III

MgCl—R₂

Column IV

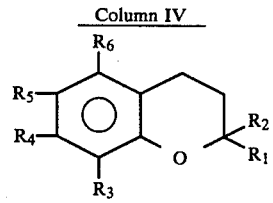

| Example | R₁ | R₂ | R₃ | R₄ | R₅ | R₆ |
|---|---|---|---|---|---|---|
| 21 | —CH₃ | —(CH₂)₃N—(CH₃)₂ | —H | —Cl | —H | —H |
| 22 | —CH₃ | —(CH₂)₃N—(CH₃)₂ | —H | —Br | —H | —H |
| 23 | —CH₃ | —(CH₂)₃N—(CH₃)₂ | —H | —CH₃ | —H | —H |
| 24 | —CH₃ | —(CH₂)₃N—(CH₃)₂ | —H | —CH₂CH₃ | —H | —H |
| 25 | —CH₃ | —(CH₂)₃N—(CH₃)₂ | —H | —H | —Cl | —H |
| 26 | —CH₃ | —(CH₂)₃N—(CH₃)₂ | —H | —H | —Br | —H |
| 27 | —CH₃ | —(CH₂)₃N—(CH₃)₂ | —H | —H | —CH₃ | —H |
| 28 | —CH₃ | —(CH₂)₃N—(CH₃)₂ | —H | —H | —CH₂CH₃ | —H |
| 29 | —CH₃ | —(CH₂)₃N—(CH₃)₂ | —H | —H | —H | —CH₃ |
| 30 | —CH₃ | —(CH₂)₃N—(CH₃)₂ | —CH₃ | —H | —H | —H |
| 31 | —CH₃ | —(CH₂)₃N—(CH₃)₂ | —CH₃ | —CH₃ | —H | —H |
| 32 | —CH₃ | —(CH₂)₃N—(CH₃)₂ | —H | —CH₃ | —CH₃ | —H |
| 33 | —CH₃ | —(CH₂)₃N—(CH₃)₂ | —CH₃ | —Cl | —CH₃ | —H |
| 34 | —H | —(CH₂)₃N—(CH₃)₂ | —H | —H | —H | —H |
| 35 | —CH₂—CH₃ | —(CH₂)₃N—(CH₃)₂ | —H | —H | —H | —H |
| 36 |  | —(CH₂)₃N—(CH₃)₂ | —H | —H | —H | —H |
| 37 |  | —(CH₂)₃N—(CH₃)₂ | —H | —H | —H | —H |
| 38 |  | —(CH₂)₃N—(CH₃)₂ | —H | —H | —H | —H |
| 39 |  | —(CH₂)₃N—(CH₃)₂ | —H | —H | —H | —H |
| 40 | —H | —(CH₂)₃N—(CH₃)₂ | —H | —H | —H | —H |
| 41 | —H | —(CH₂)₂—N(H)—CH₃ | —H | —H | —H | —H |
| 42 | —H | —CH₂—N(H)—CH₃ | —H | —H | —H | —H |
| 43 | —H | 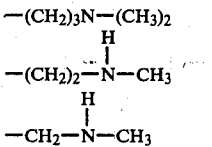 | —H | —CH₃ | —H | —H |
| 44 | —H |  | —H | —CH₃ | —H | —H |
| 45 | —H | 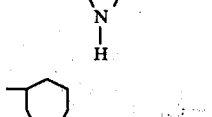 | —H | —CH₃ | —H | —H |
| 46 | —H |  | —H | —CH₃ | —H | —H |
| 47 | —H | 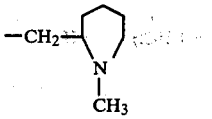 | —H | —CH₂Cl | —H | —H |
| 48 | —H |  | —H | —CHCl₂ | —H | —H |
| 49 | —H |  | —H | —CCl₃ | —H | —H |
| 50 | —H |  | —H | —H | CH₂Cl | —H |
| 51 | —H | 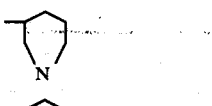 | —H | —CH₃ | —H | —H |

-continued

| Example | R$_1$ | R$_2$ | R$_3$ | R$_4$ | R$_5$ | R$_6$ |
|---|---|---|---|---|---|---|
| 52 | —H | —(CH$_2$)$_2$—[pyrrolidinyl, N—CH$_2$(CH$_2$)$_7$CH$_3$] | —H | —CH$_3$ | —H | —H |
| 53 | —CH$_3$ | —CH$_2$—[pyrrolidinyl, N—CH$_2$(CH$_2$)$_7$CH$_3$] | —H | —CH$_3$ | —H | —H |
| 54 | —CH$_3$ | —CH$_2$—[pyrrolidinyl, N—CH$_2$(CH$_2$)$_7$CH$_3$] | —H | —Cl | —H | —H |
| 55 | —CH$_3$ | —CH$_2$—[pyrrolidinyl, N—CH$_2$(CH$_2$)$_7$CH$_3$] | —H | —Br | —H | —H |
| 56 | —CH$_3$ | —CH$_2$—[pyrrolidinyl, N—CH$_2$(CH$_2$)$_7$CH$_3$] | —H | —Br | —Br | —H |
| 57 | —CH$_3$ | —CH$_2$—[pyrrolidinyl, N—CH$_2$(CH$_2$)$_7$CH$_3$] | —H | —CH$_3$ | —Cl | —H |
| 58 | —CH$_3$ | —CH$_2$—[pyrrolidinyl, N—CH$_2$(CH$_2$)$_7$CH$_3$] | —H | —CH$_2$Cl | —CH$_3$ | —H |
| 59 | —CH$_3$ | —CH$_2$—[pyrrolidinyl, N—CH$_2$(CH$_2$)$_7$CH$_3$] | —H | —H | —CH$_2$Cl | —H |
| 60 | —CH$_3$ | —CH$_2$—[pyrrolidinyl, N—CH$_2$(CH$_2$)$_7$CH$_3$] | —H | —H | —CHCl$_2$ | —H |
| 61 | —CH$_3$ | —CH$_2$—[pyrrolidinyl, N—CH$_2$(CH$_2$)$_7$CH$_3$] | —H | —H | —CHCl$_2$ | —H |
| 62 | —CH$_3$ | —CH$_2$—[pyrrolidinyl, N—CH$_2$(CH$_2$)$_7$CH$_3$] | —H | —CCl$_3$ | —H | —H |

EXAMPLE 63–75

By following the procedure of Example 4 but substituting a compound of Column I in place of 2,5-dimethyloxybenzaldehyde and a compound of Column II in place of acetone and a compound of Column III in place of the grignard reagent of N-methyl-4-chloropiperidine hydrochloride and using a compound of Column IV in place of acetic anhydride then a product of Column V is obtained.

Column I

-continued

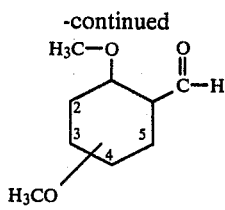

Column II

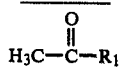

Column III

MgClR₂

Column IV

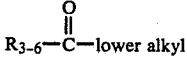

wherein $R_{3-6}$ is -o-acyl.

Column V

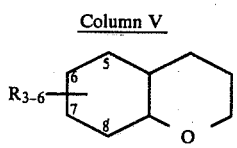

wherein $R_{3-6}$ is -o-acyl.

EXAMPLES 76-92

By following the procedure of Example 17 but substituting a compound of Column I in place of 2-hydroxy-5-methoxybenzaldehyde and a compound of Column II in place of vinyl pyridine then a product of Column III is obtained.

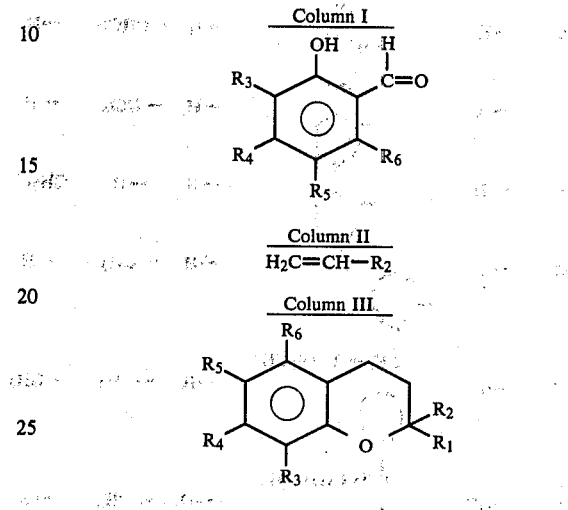

| Example | $R_1$ | $R_2$ | $R_3$ | $R_4$ | $R_5$ | $R_6$ |
|---|---|---|---|---|---|---|
| 63 | —CH₃ | —CH₂-(piperidine) | —H | —O-CO-CH₃ | —H | —H |
| 64 | —H | —CH₂-(piperidine) | —H | —H | —O-CO-CH₃ | —H |
| 65 | —H | —CH₂-(piperidine) | —O-CO-CH₃ | —H | —H | —H |
| 66 | —H | —CH₂-(piperidine) | —H | —O-CO-CH₂CH₃ | —H | —H |
| 67 | —H | —(CH₂)₃N(CH₃)₂ | —H | —O-CO-CH₂CH₃ | —H | —H |
| 68 | —H | —(CH₂)₂N(CH₃)₂ | —H | —O-CO-CH₃ | —H | —H |
| 69 | —H | —(CH₂)₃NH—CH₃ | —H | —O-CO-CH₃ | —H | —H |
| 70 | —C₆H₅ | —(CH₂)₃NH—CH₃ | —H | —O-CO-CH₃ | —H | —H |
| 71 | —H | —(CH₂)₃NH—CH₃ | —H | —H | —O-CO-CH₃ | —H |
| 72 | —H | —(CH₂)₃NH—CH₃ | —H | —H | —H | —O-CO-CH₃ |
| 73 | —H | —(CH₂)₃—N(CH₃)(CH₂)₈CH₃ | —H | —H | —H | —O-CO-CH₃ |
| 74 | —H | —(CH₂)₃—N(CH₃)(CH₂)₇CH₃ | —H | —H | —O-CO-CH₃ | —H |
| 75 | —H | —(CH₂)₃—N(CH₃)(CH₂)₇CH₃ | —H | —H | —O-CO-CH₃ | —O-CO-CH₃ |

| Example | R₁ | R₂ | R₃ | R₄ | R₅ | R₆ |
|---|---|---|---|---|---|---|
| 76 | —H |  | —H | —CH₃ | —H | —H |
| 77 | —H |  | —H | —CH₂Cl | —H | —H |
| 78 | —H |  | —H | —CHCl₂ | —H | —H |
| 79 | —H |  | —H | —CCl₃ | —H | —H |
| 80 | —H |  | —H | —H | CH₂Cl | —H |
| 81 | —H |  | —H | —CH₃ | —H | —H |
| 82 | —H |  | —H | —CH₃ | —CH₃ | —H |
| 83 | —H |  | —H | —CH₃ | —H | —H |
| 84 | —H |  | —H | —Cl | —H | —H |
| 85 | —H |  | —H | —Br | —H | —H |
| 86 | —H |  | —H | —Br | —Br | —H |
| 87 | —H |  | —H | —CH₃ | —Cl | —H |
| 88 | —H |  | —H | —CH₂Cl | —CH₃ | —H |
| 89 | —H |  | —H | —H | —CH₂Cl | —H |
| 90 | —H |  | —H | —H | —CHCl₂ | —H |
| 91 | —H |  | —H | —CHCl₂ | —H | —H |

| Example | R₁ | R₂ | R₃ | R₄ | R₅ | R₆ |
|---|---|---|---|---|---|---|
| 92 | —H | 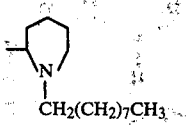 | | —H | —CCl₃ | —H | —H |

What is claimed is:
1. A compound of formula

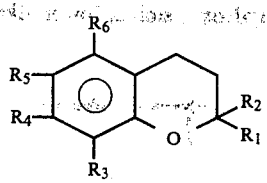

wherein $R_1$ is hydrogen, lower alkyl, substituted phenyl wherein the substituent is one or two halogen, lower alkyl, or lower alkoxy groups, phenyl, phenyl-lower alkyl, substituted phenyl-lower alkyl wherein the substituent is one or two halogen, lower alkyl, or lower alkoxy groups, or lower alkyl-amino-lower alkyl;

$R_2$ is

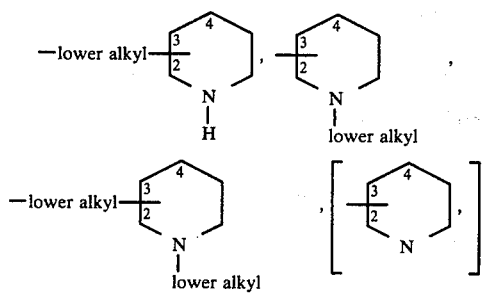

$R_3$, $R_4$, $R_5$ and $R_6$ each is independently selected from hydrogen, hydroxy, amino, lower alkanoyloxy, —O-lower alkyl,

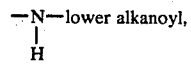

halogen, lower alkyl, or halo substituted lower alkyl; and salts and hydrates thereof.

2. The compound of claim 1 wherein $R_4$ and $R_6$ are hydrogen.

3. The compound of claim 2 wherein $R_3$ and $R_5$ are hydrogen, hydroxy, amino, lower alkanoyloxy or —O-lower alkyl.

4. The compound of claim 3, 4-(3,4-dihydro-2-methyl-2H-benzopyran-2-yl)-1-methylpiperidine, hydrochloride, hydrate (1:1:1).

5. The compound of claim 3, 3,4-dihydro-2-methyl-2-(1-methyl-4-piperidinyl)-2H-1-benzopyran-6-ol, acetate ester, hydrochloride (1:1).

6. The compound of claim 3, 3,4-dihydro-N,N-dimethyl-2-(1-methyl-4-piperidinyl)-2H-1-benzopyran-2-propanamine, hydrochloride (1:2).

7. The compound of claim 3, 3,4-dihydro-2-methyl-2-(2-piperidinylmethyl)-2H-1-benzopyran-6-ol, hydrobromide (1:1).

8. The compound of claim 3, 2-[(3,4-dihydro-2-methyl-2H-benzopyran-2-yl)methyl]piperidine, oxalate salt (2:1).

9. The compound of claim 3, 3,4-dihydro-2-methyl-2-[(1-nonyl-2-piperidinyl)methyl]-2H-1-benzopyran-6-ol, barbituric acid salt (1:1).

10. The compound of claim 3, 2-[(3,4-dihydro-2-methyl-2H-1-benzopyran-2-yl)methyl]-1-nonylpiperidine, barbituric acid salt (1:2).

11. A method for treatment of inflammation of joints in mammalian species in need thereof which comprises administering to said mammal an effective amount of a compound having the formula

wherein $R_1$ is hydrogen, lower alkyl, substituted phenyl wherein the substituent is one or two halogen, lower alkyl, or lower alkoxy groups, phenyl, phenyl-lower alkyl, substituted phenyl-lower alkyl wherein the substituent is one or two halogen, lower alkyl, or lower alkoxy groups, or lower alkyl-amino-lower alkyl;

$R_2$ is

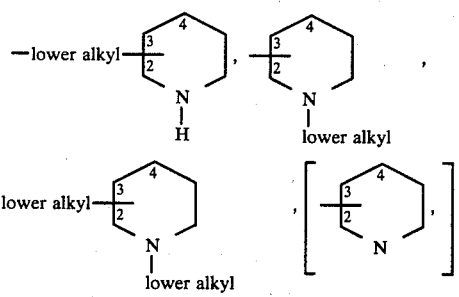

$R_3$, $R_4$, $R_5$ and $R_6$ each is independently selected from hydrogen, hydroxy, amino, lower alkanoyloxy, —O-lower alkyl,

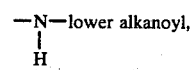

halogen, lower alkyl, or halo substituted lower alkyl; and salts and hydrates thereof.

12. A method of treatment of allergy in mammalian species in need thereof which comprises administering to said mammal an effective amount of a compound of the formula

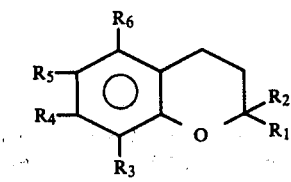

wherein

R₁ is hydrogen, lower alkyl, substituted phenyl wherein the substituent is one or two halogen, lower alkyl, or lower alkoxy groups, phenyl, phenyl-lower alkyl, substituted phenyl-lower alkyl wherein the substituent is one or two halogen, lower alkyl, or lower alkoxy groups or lower alkyl-amino-lower alkyl;

R₂ is

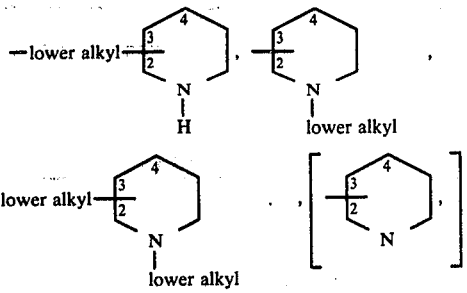

R₃, R₄, R₅ and R₆ each is independently selected from hydrogen, hydroxy, amino, lower alkanoyloxy, —O-lower alkyl,

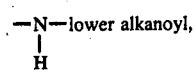

halogen, lower alkyl, or halo substituted lower alkyl; and salts and hydrates thereof.

* * * * *

UNITED STATES PATENT AND TRADEMARK OFFICE
CERTIFICATE OF CORRECTION

PATENT NO. : 4,321,270
DATED : March 23, 1982
INVENTOR(S) : Joseph E. Sundeen

It is certified that error appears in the above—identified patent and that said Letters Patent is hereby corrected as shown below:

Column 1, line 12, the structure should read as follows:

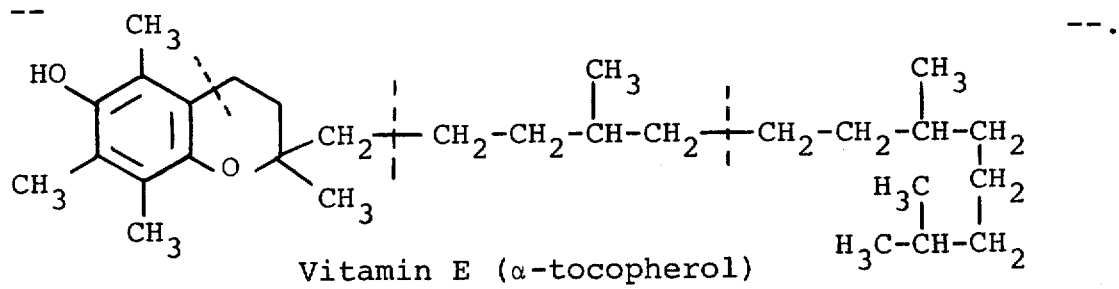

Vitamin E (α-tocopherol)

Column 9, line 36, after "[2-" insert --(2- --.
Column 12, line 21, "if" should read --is--.
Column 20, line 60, "10 m" should read --10 ml--.
Column 33, lines 38 to 43, delete the structure in brackets.
Column 34, lines 50 to 55, delete the structure in brackets.
Column 36, lines 8 to 13, delete the structure in brackets.

Signed and Sealed this

Twenty-fourth Day of August 1982

[SEAL]

Attest:

GERALD J. MOSSINGHOFF

Attesting Officer   Commissioner of Patents and Trademarks